United States Patent
Liu et al.

(10) Patent No.: US 8,633,346 B2
(45) Date of Patent: *Jan. 21, 2014

(54) PROCESS FOR PREPARING AN ALKYLATE

(75) Inventors: Zhichang Liu, Beijing (CN); Chunming Xu, Beijing (CN); Rui Zhang, Beijing (CN); Xianghai Meng, Beijing (CN); Ana Cecilia Patroni, Amsterdam (NL); Peter Anton August Klusener, Amsterdam (NL); Albertus Vincentius Petrus Van Den Bosch, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/388,491

(22) PCT Filed: Aug. 5, 2010

(86) PCT No.: PCT/EP2010/061447
§ 371 (c)(1),
(2), (4) Date: Mar. 13, 2012

(87) PCT Pub. No.: WO2011/015639
PCT Pub. Date: Feb. 10, 2011

(65) Prior Publication Data
US 2012/0165590 A1    Jun. 28, 2012

(30) Foreign Application Priority Data

Aug. 6, 2009  (WO) ................. PCT/CN2009/000884

(51) Int. Cl.
*C07C 2/56* (2006.01)

(52) U.S. Cl.
USPC ................. 585/709; 585/710; 208/251 R

(58) Field of Classification Search
None
See application file for complete search history.

(56) References Cited

U.S. PATENT DOCUMENTS

| | | | |
|---|---|---|---|
| 7,285,698 B2 | 10/2007 | Liu et al. | 585/721 |
| 7,727,925 B2 * | 6/2010 | Elomari et al. | 502/150 |
| 2004/0133056 A1 * | 7/2004 | Liu et al. | 585/721 |
| 2009/0163349 A1 * | 6/2009 | Elomari et al. | 502/26 |
| 2010/0248940 A1 * | 9/2010 | Elomari et al. | 502/20 |
| 2011/0105820 A1 * | 5/2011 | Harris | 585/722 |

* cited by examiner

Primary Examiner — Tam M Nguyen
(74) Attorney, Agent, or Firm — Charles W. Stewart

(57) ABSTRACT

The present invention provides process for preparing an alkylate comprising contacting in a reaction zone a hydrocarbon mixture comprising at least an isoparaffin and an olefin with an acidic ionic liquid catalyst under alkylation conditions to obtain an alkylate-comprising effluent, in which process: —solids are formed in the reaction zone; —a solids-comprising effluent comprising hydrocarbons and acidic ionic liquid is withdrawn from the reaction zone; and—at least part of the solids-comprising effluent is treated to remove at least part of the solids to obtain a solids-depleted effluent. The invention further provides a process for treating an acidic ionic liquid comprising at least 0.1 wt % of solids based on the total weight of the acidic ionic liquid, wherein at least part of the solids are removed.

45 Claims, 1 Drawing Sheet

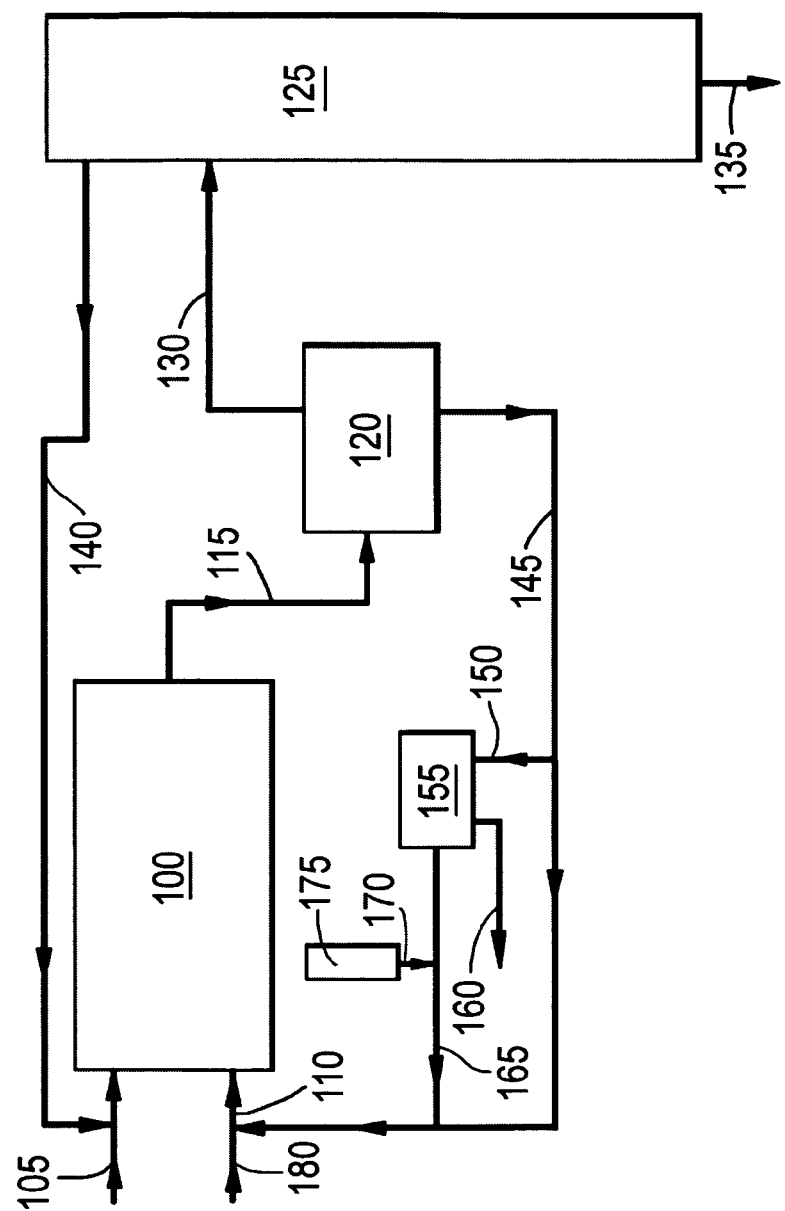

PROCESS FOR PREPARING AN ALKYLATE

PRIORITY CLAIM

The present application claims priority from PT/EP2010/061447, filed 5 Aug. 2010, which claims priority from PCT/CN2009/000884, filed 6 Aug. 2009.

FIELD OF THE INVENTION

The present invention provides a process for preparing an alkylate, and a process for treating an acidic ionic liquid.

BACKGROUND OF THE INVENTION

There is an increasing demand for alkylate fuel blending feedstock. As a fuel-blending component alkylate combines a low vapour pressure, no sulphur, olefins or aromatics with high octane properties.

Almost all alkylate is produced by reacting isobutane with butene in the presence of a suitable acidic catalyst. The most used catalysts are HF and sulphuric acid, although other catalysts such a solid acid catalyst have been reported. Recently, the alkylation of isoparaffins with olefins using an acidic ionic liquid catalysts has attracted attention as an alternative to HF and sulphuric acid catalysed alkylation processes.

In for instance U.S. Pat. No. 7,285,698 a process for manufacturing an alkylate oil is disclosed, which uses a composite ionic liquid catalyst to react isobutane with a butene. In the process of U.S. Pat. No. 7,285,698, isobutane and butene are supplied to a reactor and the alkylate is formed by contacting the reactants with an composite ionic liquid under alkylation conditions. The reactor effluent is separated and the ionic liquid phase is recycled to the reactor while the hydrocarbon phase is treated to retrieve the alkylate. Although, the process of U.S. Pat. No. 7,285,698 shows that the use of an ionic liquid catalyst allows for the preparation of a good alkylate fuel blending component, there is still a need in the art for an improved ionic liquid alkylation process.

SUMMARY OF THE INVENTION

It has been found that during operation of an ionic liquid alkylation process, solids may be formed. As the reaction progresses, these solids accumulate in the reaction zone and may lead to blockage of pathways and/or valves. This problem may be resolved by using the process according to the present invention.

Accordingly, the present invention provides a process for preparing an alkylate comprising contacting in a reaction zone a hydrocarbon mixture comprising at least an isoparaffin and an olefin with an acidic ionic liquid catalyst under alkylation conditions to obtain an alkylate-comprising effluent, in which process:
  solids are formed in the reaction zone;
  a solids-comprising effluent comprising hydrocarbons and acidic ionic liquid is withdrawn from the reaction zone; and
  at least part of the solids-comprising effluent is treated to remove at least part of the solids to obtain a solids-depleted effluent.

By removing at least part of the solids formed during the alkylation reaction, the accumulation of solids in the reaction zone may be prevented.

In another aspect, the invention provides a process for treating an acidic ionic liquid comprising at least 0.1 wt % of solids based on the total weight of the acidic ionic liquid, wherein at least part of the solids are removed from the acidic ionic liquid.

BRIEF DESCRIPTION OF THE DRAWINGS

In FIG. 1 a schematic representation is given of a process according to the invention.

DETAILED DESCRIPTION OF THE INVENTION

In the process according to the invention an alkylate is prepared by reacting an isoparaffin with an olefin. The obtained alkylate is particularly suitable for gasoline blending purposes or for use in aviation gasoline production. In the process according to the invention the isoparaffin and the olefin are provided to a reaction zone. In the reaction zone a hydrocarbon mixture comprising isoparaffin and olefin is contacted with a catalyst suitable for alkylation. The hydrocarbon mixture comprises olefin typically supplied externally, i.e. fresh olefin, and comprises isoparaffin. The isoparaffin may be externally supplied isoparaffin, i.e. fresh isoparaffin, and/or isoparaffin, which is recycled from any other part of the process. The fresh isoparaffin and olefin may be supplied to the process separately, however typically the fresh isoparaffin and the fresh olefin are provided to the reaction zone as a mixture comprising isoparaffin and olefin. In the present invention the catalyst is an acidic ionic liquid or a composite mixture comprising the ionic liquid (herein below also referred to a catalyst).

Ionic liquids are known in the art for their ability to catalyse alkylation reactions. The catalyst used in the present invention is a composite ionic liquid comprising cations derived from a hydrohalide of an alkyl-containing amine, imidazolium or pyridine. Preferably, the cations comprise nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of suitable cations include triethyl-ammonium (NEt$_3$H$^+$) and methyl-diethyl-ammonium cations (MeNEt$_2$H$^+$) or

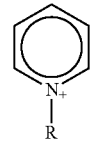

The anions of the composite ionic liquid are preferably aluminium based Lewis acids, in particular aluminium halides, preferably aluminium (III) chloride. Due to the high acidity of the aluminium chloride Lewis acid it is preferred to combine the aluminium chloride, or other aluminium halide, with a second or more metal halide, sulphate or nitrate to form a coordinate anion, in particular a coordinate anion derived from two or more metal halides, wherein at least one metal halide is an aluminium halide. Suitable further metal halides, sulphates or nitrates, may be selected from halides, sulphates or nitrates of metals selected from the group consisting of Group IB elements of the Periodic Table, Group IIB elements of the Periodic Table and transition elements of the Periodic Table. Examples or suitable metals include copper, iron, zinc, nickel, cobalt, molybdenum, or platinum. Preferably, the metal halides, sulphates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

As mentioned hereinabove, the hydrocarbon mixture comprising isoparaffin and olefin is contacted with the catalyst in the reaction zone. The hydrocarbon mixture is mixed in the reaction zone with the catalyst to form a reaction mixture. As the reaction progresses the reaction mixture will, besides hydrocarbon reactants and acidic ionic liquid, additionally comprise products. Mixing of the hydrocarbon mixture and the catalyst may be done by any suitable means for mixing two or more liquids, including dynamic and static mixers. In contact with the catalyst, the isoparaffins and olefins react under alkylation conditions to form an alkylate. The formed alkylate is obtained from the reaction zone in the form of an alkylate-comprising effluent. The alkylate-comprising effluent still comprises a substantial amount of unreacted isoparaffin. Therefore, part of the alkylate-comprising effluent may be recycled to the reaction zone to maintain a high ratio of isoparaffin to olefin in hydrocarbon mixture in the reaction zone. At least part of the alkylate-comprising effluent of the reaction zone is separated in a separator unit into a hydrocarbon-rich phase and an acidic ionic liquid catalyst-rich phase. Reference, herein to a hydrocarbon-rich phase is to a phase comprising more than 50 mol % of hydrocarbons, based on the total moles of hydrocarbon and acidic ionic liquid catalyst. Reference, herein to an acidic ionic liquid catalyst-rich phase is to a phase comprising more than 50 mol % of acidic ionic liquid catalyst, based on the total moles of hydrocarbon and acidic ionic liquid catalyst. Due to the low affinity of the acidic ionic liquid for hydrocarbons and the difference in density between the hydrocarbons and the acidic ionic liquid catalyst, the separation is suitably done using for example well known settler means, wherein the hydrocarbons and catalyst separate into an upper predominantly hydrocarbon phase and lower predominantly catalyst phase or by using any other suitable liquid/liquid separator. Such liquid/liquid separators are known to the skilled person and include cyclone and centrifugal separators. The catalyst phase is generally recycled back to the reactor. As the hydrocarbon phase still comprises significant amounts of unreacted isoparaffin, part of the hydrocarbon phase may be recycled to the reactor to maintain a high isoparaffin to olefin ratio in the reaction zone. However, at least part of the hydrocarbon phase is treated and/or fractionated to retrieve an alkylate-comprising product.

It has been observed that during the alkylation reaction solids are formed in the reaction zone. Reference, herein to solids is to non-dissolved solid particles. The solids predominantly consist out of metals, metal compounds and/or metal salts which were originally comprised in the acidic liquid catalyst. Preferably, the solids comprise at least 10 wt % metal, i.e. either in metallic, covalently bound or ionic form, based on the total weight of the solids, wherein the metal is a metal that was introduced to the process as part of the acidic ionic liquid catalyst. The solids may also comprise components, which were introduced into the reaction mixture as contaminants in the hydrocarbon mixture or the acidic ionic liquid. Alternatively, the solids may be the product of a chemical reaction involving any of the above-mentioned compounds.

The solids may have any size, however it was found that the solids typically have an average size of in the range of from 0.1 to 10 μm. In particular, at least 50% of the solids have a particle size below 5 μm, more particular 80% of the solids have a particle size below 5 μm based on the total number of solid particles.

Although, during mixing these solids are dispersed throughout the reaction mixture, upon separation of the alkylate-comprising effluent it has been found that the solids, i.e. to a large extent, accumulate in the acidic ionic liquid catalyst-rich phase. This is due to the high density of the solids. The catalyst-rich phase is subsequently recycled to the reaction zone to become part of the reaction mixture in the reaction zone. As a result, the solids accumulate in the reaction zone, resulting in undesirably high solids content in the reaction zone. A high solids content in the reaction zone may for instance result in blockage of pathways or valves in the reactor zone and pipes to and from the separation unit, due to precipitation of solids. In addition, at high solids content the solids may agglomerate to form large aggregates, resulting in increased blockage risk.

In the present invention, at least part of the solids are removed from the reaction zone. Preferably, solids are removed from the reaction zone to an extent that the reaction mixture, i.e. a mixture comprising hydrocarbon reactants, acidic ionic liquid and products, comprises at most 5 wt % of solids, preferably at most 2 wt % of solids, based on the total weight of the acidic ionic liquid in the reactor. It is not required to remove all solids from the reaction zone, preferably, solids are removed from the reaction zone to an extent that the reaction zone comprises in the range of from 0.05 to 5 wt %, more preferably of from 0.1 to 2 wt % of solids, based on the total weight acidic ionic liquid in the reaction zone.

The solids may be removed from the reaction zone at any time or place in the process. It is possible to remove the solids from the reaction mixture directly inside the reaction zone. However, preferably, at least part of the reaction mixture is withdrawn from the reaction zone as a solids-comprising effluent. This solids-comprising effluent comprises next to the solid also hydrocarbons and acidic ionic liquid, wherein the hydrocarbons typically include isoparaffins and alkylate. Subsequently, at least part of the solids-comprising effluent is treated to remove at least part of the solids. After the treatment to remove solids a solids-depleted effluent is obtained.

Preferably, at least part of the solids-depleted effluent is recycled to the reactor.

The solids-comprising effluent as withdrawn from the reaction may be treated to remove solids. However preferably, the solids-comprising effluent is first separated into a catalyst-rich phase and a hydrocarbon-rich phase and the catalyst-rich phase is subsequently treated to remove solids. As mentioned herein above, the solids accumulate in the catalyst-rich phase formed in a typical separator unit Preferably, the solids-comprising effluent is or is at least part of the alkylate-comprising effluent, which is sent to the separation unit. In this case the alkylate-comprising effluent may be treated to remove solids prior to the separation unit. However, as the solids accumulate in the catalyst-rich phase, it is preferred to first separate the alkylate-comprising effluent into a first part comprising a catalyst-rich phase and a second part comprising a hydrocarbon-rich phase and subsequently remove the solids from the catalyst-rich phase. Subsequently, the, solids-depleted, catalyst can preferably be reintroduced into the reaction zone.

The solids may be removed by any suitable means for removing solids from liquids, including but not limited to filtration, precipitation and centrifugation processes. Such processes are well known in the art.

Due to the specific nature of ionic liquids it is preferred that the removal of the solids is performed at such a temperature that the acidic ionic liquid catalyst is liquid. In particular, it is preferred to remove the solids at a temperature in the range of from 5 to 80° C., more preferably of from 20 to 60° C., while ensuring that the temperature is such that the ionic liquid remains a liquid. By removing the solids at elevated temperatures, the viscosity of the ionic liquid is lower while the density is reduced, which may be beneficial in view of decreased time and power input required to obtained separation of the solids from the liquid.

The solids may be removed form the process in any form, typically the solids will be removed in the form of a slurry of solids. Such a slurry may comprise next to the solids for instance some residual acidic ionic liquid. The slurry may be further treated to extract the residual acidic ionic liquid. This is preferably done using a liquid-liquid extraction process with a suitable solvent. Due to the virtual absence of an ionic liquid vapour pressure, the solvent can be easily recovered by for instance evaporation and subsequent condensation. The recovered solvent can be reused.

Although, it is believed that part of the catalyst is lost when forming the solids, the catalyst alkylation performance is not significantly affected. Loss of catalyst due to solids formation merely means that a small fraction of the total catalyst inventory is inactivated or lost, while the remainder of the catalyst remains unaffected.

Optionally, catalyst can be contacted with an acid, preferably a hydrogen halide, more preferably hydrogen chloride, to rejuvenate the catalyst. This can be done by introducing, i.e. adding, hydrogen chloride into the process. Preferably, at least part of the acidic ionic liquid catalyst in the solids-comprising effluent is rejuvenated. Preferably, at least part of the rejuvenated acidic ionic liquid catalyst is recycled to the reaction zone. Preferably, the acidic ionic liquid catalyst is first separated from the solids-comprising effluent and/or solids-depleted effluent, prior to the rejuvenation.

The acidic ionic liquid catalyst-rich phase which is separated from the solids-comprising effluent and/or solids-depleted effluent may still contain some dissolved hydrocarbons. These may be removed, however this is not necessary. By contacting the catalyst with hydrogen chloride after separation from the hydrocarbon phase, undesired chlorination of hydrocarbons is reduced. The hydrogen chloride reacts with the acidic ionic liquid catalyst. Hydrogen chloride is added until no hydrogen chloride is consumed any longer, i.e. until saturation. Hydrogen chloride consumption can be followed by monitoring the pressure. Preferably, the addition of hydrogen chloride is done in regular steps, while measuring the pressure in between each addition step. By adding the hydrogen chloride in small steps the creation of an undesired hydrogen chloride gas cap upon saturation is reduced.

The addition of hydrogen chloride may be done by injecting the hydrogen chloride into one or more units or into one or more streams passing from one unit to the next. Hydrogen chloride addition may for instance be done using a venturi absorber, preferably a venturi absorber located downstream from the means for removing solids.

As mentioned herein above, although some gaseous hydrogen chloride in the reaction zone may be tolerated, it is undesired to accumulate unreacted gaseous hydrogen chloride in the reaction system as a result of over-saturation of the acidic ionic liquid with hydrogen chloride. Residual gaseous hydrogen chloride may be purged from the reaction system by for instance flushing with an inert gas such as nitrogen. However, such process would require additional means for providing nitrogen gas and subsequent storage and treatment of hydrogen chloride-contaminated nitrogen gas. In addition, part of the hydrogen chloride is provided for rejuvenation is lost. Preferably, such hydrogen chloride accumulation is reduced by mixing additional spent acidic ionic liquid catalyst, e.g. in the form of a spent catalyst-comprising stream, into the rejuvenated acidic ionic liquid catalyst comprising recycled effluent, i.e. the recycled effluent comprising added hydrogen chloride. Reference, herein to spent acidic ionic liquid catalyst is to an acidic ionic liquid catalyst, which has been used as a catalyst in a chemical reaction and has not yet been rejuvenated with hydrogen chloride. By allowing the spent acidic ionic liquid to react with the gaseous hydrogen chloride present due to initial over-saturation, the remaining hydrogen chloride may be consumed. The spent ionic liquid catalyst may be introduced from an external source, however it is also possible to allow part of the ionic liquid catalyst phase or catalyst-comprising recycled effluent to bypass the rejuvenation and subsequently mix the rejuvenated and bypassed streams.

The solids, which are removed from the process may be discarded, however it is preferred to reuse the components in the solids, for example in the preparation of fresh acidic ionic liquid catalyst.

In the process according to the invention, an isoparaffin and an olefin are reacted to form an alkylate by contacting the hydrocarbon mixture comprising isoparaffin and olefin with the catalyst under alkylation conditions.

Preferably, the hydrocarbon mixture comprises at least isobutane, isopentane or a mixture thereof as an isoparaffin. The hydrocarbon mixture preferably comprises at least an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

Isoparaffins and olefins are supplied to the process in a molar ratio, which is preferably 1 or higher, and typically in the range of from 1:1 to 40:1, more preferably 1:1 to 20:1. In the case of continuous reaction, excess isoparaffin can be recycled for reuse in the hydrocarbon mixture.

The alkylation conditions (or process conditions) are those known in the art for HF and sulphuric acid alkylation. Actual operational process conditions are among others dependent of the exact composition of the hydrocarbon mixture and catalyst.

The temperature in the reactor is preferably in the range of from −20 to 100° C., more preferably in the range of from 0 to 50° C. In any case the temperature must be high enough to ensure that the ionic liquid catalyst is in the liquid state.

To suppress vapour formation in the reactor, the process is performed under pressure, preferably the pressure in the reactor is in the range of from 0.1 to 1.6 MPa.

Preferably, the acidic ionic liquid catalyst to hydrocarbon ratio in the reaction zone is at least 0.5, preferably 0.9 more preferably at least 1. Preferably, the acidic ionic liquid catalyst to hydrocarbon ratio in the reaction zone is in the range of from 1 to 10.

The hydrocarbon mixture may be contacted with the catalyst in any suitable alkylation reactor. The hydrocarbon mixture may be contacted with the catalyst in a semi-continues or continuous process.

Part of the hydrocarbon-rich phase obtained after phase separating the alkylate-comprising effluent in a hydrocarbon-rich phase and a catalyst-rich phase may be recycled to the reaction zone or be combined with the hydrocarbon mixture or fresh isoparaffin and/or olefin prior to providing such to the reaction zone. The hydrocarbon-rich effluent still comprises substantial amounts of isoparaffin. By recycling part of the hydrocarbon-rich phase back to the reaction zone it is possible to maintain a high molar ratio of isoparaffin to olefin the reaction zone. At least part of the hydrocarbon-rich phase obtained after phase separating the alkylate-comprising effluent in a hydrocarbon-rich phase and a catalyst-rich phase, may be treated to fractionate the hydrocarbon-rich phase and to retrieve the alkylate and optionally other components in the hydrocarbon phase, such as unreacted isoparaffin or n-paraffins.

The hydrocarbon-rich phase may be treated by any suitable way to fractionate a hydrocarbon stream, such a distillation.

Following the fractionation, the obtained alkylate or alkylate comprising product may be used to prepare avgas or as a blending component for gasoline. As mentioned, the hydrocarbon-rich phase may also comprise isoparaffin. Preferably, such isoparaffin is at least partly reused to form part of the isoparaffin feed provided to the process. This may be done by recycling at least part of the isoparaffin, or a stream comprising isoparaffin obtained from the fractionation of the hydrocarbon-rich phase, and combining it with the isoparaffin feed to the process.

In another aspect the invention also provides a process for treating an acidic ionic liquid comprising at least 0.05 wt %, preferably 0.1 wt % of solids based on the total weight of the acidic ionic liquid, wherein at least part of the solids are removed from the acidic ionic liquid. Preferably, the acidic ionic liquid comprising solids was used as a catalyst in a chemical reaction, more preferably an alkylation reaction, even more preferably an isoparaffin/olefin alkylation reaction. Preferably, the acidic ionic liquid is an ionic liquid as described herein above for the process for preparing an alkylate according to the invention. Preferably, the solids are removed via the same methods as described herein above for the process for preparing an alkylate according to the invention and at the same temperatures.

DETAILED DESCRIPTION OF THE DRAWINGS

In FIG. 1 a schematic representation is given of a process according to the invention.

In FIG. 1, a mixture, comprising olefin and isoparaffin is provided to reactor 100 through line 105. Acidic ionic liquid catalyst is also provided to reaction zone 100 through line 110. In reaction zone 100, the hydrocarbon mixture and catalyst are mixed under alkylation conditions. Through line 115, a solids-comprising effluent comprising hydrocarbons and acidic ionic liquid is withdrawn from the reaction zone. Part of this effluent may be directly recycled to the reactor or combined with line 105 via a recycle line (not shown). At least part of the effluent is supplied to liquid/liquid separation unit 120, e.g. a settler unit. In liquid/liquid separation unit 120, a hydrocarbon-rich phase and catalyst-rich phase separate under influence of gravity or centrifugal forces. Part of the hydrocarbon-rich phase may be directly recycled to the reactor or combined with line 105 via a recycle line (not shown). At least part of the hydrocarbon-rich phase is provided to fractionator 125 through line 130. From the bottom of fractionator 125, an alkylate-comprising product is retrieved through line 135. The alkylate-comprising product can be used for instance for fuel blending purposes. Additionally, an isoparaffin-comprising stream is retrieved from fractionator 125, which is recycled via line 140 to become part of the mixture in line 105. Other hydrocarbon-comprising streams (not shown) may also be retrieved from fractionator 125.

The acidic ionic liquid catalyst phase can be recycled via line 145 to reactor 100. Part or all of the catalyst can be diverted from line 145 by line 150 to centrifuge 155. In centrifuge 155, solids are removed from the acidic ionic liquid catalyst phase under influence of the centrifugal forces, and are retrieved via line 160. The remaining acidic ionic liquid catalyst phase exits centrifuge 155 via line 165. Optionally, hydrochloride gas is provided to the acidic ionic liquid catalyst phase via line 170 from gas container 175. Optionally, a mixing device (not shown), e.g. a venturi absorber, is used to mix the hydrogen chloride gas into line 165. By allowing part of the catalyst to bypass the hydrogen chloride rejuvenation via line 145, any remaining gaseous hydrogen chloride may react with the ionic liquid catalyst in line 145 when lines 165 and 145 come together. It is also possible to provide a bypass (not shown) around the intersection of lines 165 and 170. In this way solids may be removed also from the ionic liquid catalyst, which is not rejuvenated.

The acidic ionic liquid catalyst phase is subsequently directed back to reaction zone 100. If necessary additional fresh acidic ionic liquid catalyst or externally supplied spent acidic ionic liquid catalyst can be provided to reaction zone 100 via line 180.

EXAMPLES

The invention is illustrated by the following non-limiting examples.

Alkylation Process

An alkylation process was performed in three separate runs to mimic regular solids removal. In between each run the acidic ionic liquid catalyst was separated from the hydrocarbon phase and treated by removing solids and adding hydrogen chloride gas. The treated acidic ionic liquid catalyst was subsequently used in the following run.

The catalyst used was an ionic liquid catalyst comprising a coordinate anion derived from aluminium(III) chloride and copper(I) chloride) (ex China University of Petroleum Beijing).

A hydrocarbon mixture of isobutane and butenes was provided together with the acidic ionic liquid catalyst to the alkylation reactor. The reactor had a volume of 0.4 litre.

The effluent of the alkylation reactor was separated in a settler and part of the hydrocarbon phase was sent to a fractionator, while the remainder of the hydrocarbon phase was recirculated to the reactor. The alkylate was obtained from the bottom of the fractionator and tested to determine the motor RON and MON values.

An isobutane-comprising stream was recycled from the fractionator back to the hydrocarbon mixture.

The acidic ionic liquid catalyst phase obtained from the settler was recycled to the reactor. Periodically, i.e. between the runs, the acidic ionic liquid catalyst phase obtained from the settler was redirected to a disk centrifuge and centrifuged at 20000 rpm for 1 hour at a temperature of 50° C. The weight of solids produced was recorded. Following the solids removal, hydrogen chloride gas was added to the treated acidic ionic liquid catalyst at a pressure of approximately 5 bar at a temperature of 35° C., until no hydrogen chloride was consumed any more. The amount of hydrogen chloride consumed was recorded. The reaction condition and obtained results are listed in Table 1. It will be clear that in case no solids removal would have taken place approximately 1.5 kg of solids would have accumulated in the reactor. By removing the solids, solids content is significantly reduced and the alkylate quality remains high. The observed differences in the obtained alkylate properties are caused by the differences in the alkylation temperature and isoparaffin to olefin ratio.

TABLE 1

| Run | | 1 | 2 | 3 |
|---|---|---|---|---|
| Reaction temperature, | ° C. | 35.7 | 41.0 | 35.9 |
| isobutane/butene ratio in feed* | mol/mol | 5.3 | 11.3 | 11.6 |
| Ionic liquid/hydrocarbon ratio | vol/vol | 1.08 | 1.06 | 1.06 |
| Feed flow rate, | kg/h | 1.5 | 1.9 | 1.9 |
| Runtime, | h | 67 | 52 | 53 |
| Fresh C4 feed, | kg | 101.8 | 99.5 | 101.6 |
| Fresh feed composition | mol % | | | |
| propane | | 0.1 | 0.1 | 0.1 |
| isobutane | | 56.7 | 50.6 | 52.1 |
| n-butane | | 8.7 | 10.9 | 9.0 |
| 1-butene | | 1.6 | 2.2 | 1.6 |
| 2-butene (trans) | | 20.8 | 22.0 | 23.4 |
| 2-butene (cis) | | 8.9 | 10.5 | 10.0 |
| i-butene | | 3.0 | 3.2 | 3.2 |
| Alkylate, | kg | 73.3 | 81.6 | 90.4 |
| Engine tested RON | — | 90.5 | 94.0 | 95.0 |
| Engine tested MON | — | 90.2 | 91.8 | 92.7 |
| Total solids** | g | 729.3 | 435 | 376 |
| Hydrogen chloride consumption | g | 143 | 95 | 104 |

*isobutane/butene ratio, i.e. the isobutane/butene ratio in the mixture of fresh feed and the isobutane recycled from the fractionator
**total weight of the solids slurry Solids Analysis The solids removed from the acidic ionic liquid catalyst phase were analysed. The size distribution was determined using a laser particle size analyser.

The results are shown in Table 2.

TABLE 2

| Run | | 1 | 2 | 3 |
|---|---|---|---|---|
| Percentage of particles having a diameter below 5μ | % | 99 | 99 | 99 |
| Percentage of particles having a diameter below 3μ | % | 80 | 81 | 80 |

What is claimed is:

1. A process for preparing an alkylate, where the process comprises: contacting in a reaction zone a hydrocarbon mixture comprising at least an isoparaffin and an olefin with an acidic ionic liquid catalyst under alkylation conditions to form an alkylate and solids in the reaction zone;
   withdrawing an alkylate-comprising effluent, comprising alkylate, solids and acidic ionic liquid catalyst, from the reaction zone; and
   treating at least part of the alkylate-comprising effluent to remove at least part of the solids to obtain a solids-depleted effluent, wherein the amount of solids removed from the alkylate-comprising effluent is sufficient to maintain the concentration of solids in the reaction zone at the most 5 wt %, based on the total weight of the acidic ionic liquid catalyst in the reaction zone.

2. A process according to claim 1, wherein at least part of the solids-depleted effluent is recycled to the reaction zone.

3. A process according to claim 2, wherein the alkylate-comprising effluent is separated into a catalyst-rich phase and a hydrocarbon-rich phase and the catalyst-rich phase is treated to remove solids in an amount sufficient to maintain the concentration of solids in the reaction zone from 0.05 to 5 wt %, based on the total weight of the acidic ionic liquid catalyst in the reaction zone.

4. A process according to claim 2, wherein solids are removed by centrifugation to an extent that the reaction zone comprises from 0.05 to 5 wt % of solids, based on the total weight of the acidic ionic liquid catalyst in the reaction zone.

5. A process according to claim 4, wherein solids are removed from the reaction zone to an extent that the reaction zone comprises at most 2 wt % of solids, based on the total weight of the acidic ionic liquid catalyst in the reaction zone.

6. A process according to claim 5, wherein at least part of the acidic ionic liquid catalyst in the alkylate-comprising effluent is rejuvenated by addition of hydrogen chloride and recycled to the reaction zone.

7. A process according to claim 6, wherein subsequent to the addition of hydrogen chloride the acidic ionic liquid catalyst with added hydrogen chloride is mixed with a spent acidic ionic liquid catalyst-comprising stream.

8. A process according to claim 7, wherein solids are removed from the at least part of solids-comprising effluent at a temperature in the range of from 5 to 80° C.

9. A process according to claim 8, wherein at least part of the alkylate-comprising effluent is fractionated to obtain an alkylate-comprising product.

10. A process according to claim 9, wherein hydrocarbon mixture comprises isobutane and/or isopentane.

11. A process according to claim 10, wherein the hydrocarbon mixture comprises an olefin comprising in the range of from 3 to 6 carbon atoms.

12. A process for treating an acidic ionic liquid comprising at least 0.1 wt % of solids based on the total weight of the acidic ionic liquid, wherein the acidic ionic liquid comprising solids was used as a catalyst in an alkylation reaction in a reaction zone and at least part of the solids are removed from the acidic ionic liquid sufficient to maintain the concentration of solids in the reaction zone at the most 5 wt %, based on the total weight of the acidic ionic liquid in the reaction zone.

13. A process according to claim 12, wherein the acidic ionic liquid catalyst is a composite ionic liquid comprising of cations derived from a hydrohalide of an alkyl-containing amine or pyridine, anions being composite coordinate anions derived from two or more metal halides, wherein at least one metal halide is an aluminium halide and any further metal halide is a halide of a metal selected from the group consisting of Group IB elements of the Periodic Table, Group IIB elements of the Periodic Table and transition elements of the Periodic Table.

14. A process according to claim 13, wherein the catalyst comprises aluminium chloride and copper (I) chloride or copper (II) chloride.

15. A process according to claim 1, wherein the solids are removed from at least part of the alkylate-comprising effluent by filtration, precipitation and/or centrifugation processes.

16. A process for preparing an alkylate, wherein said process comprises:
   contacting in a reaction zone and under alkylation conditions a hydrocarbon mixture comprising at least an isoparaffin and an olefin with an acidic ionic liquid catalyst to form within said reaction zone alkylate and solids;
   withdrawing from said reaction zone an alkylate-comprising effluent, comprising alkylate, solids and acidic ionic liquid catalyst;

separating said alkylate-comprising effluent into a hydrocarbon-rich phase and an acidic ionic liquid catalyst-rich phase;
fractionating at least part of said hydrocarbon-rich phase to provide an alkylate-comprising product and an isoparaffin-comprising stream; and
treating at least part of said acidic ionic liquid catalyst-rich phase to remove at least part of the solids therefrom and to obtain a solids-depleted effluent, wherein the amount of solids removed from the acidic ionic liquid catalyst-rich phase is sufficient to maintain the concentration of solids in the reaction zone at the most 5 wt %, based on the total weight of the acidic ionic liquid catalyst in the reaction zone.

17. A process as recited in claim 16, further comprising:
recycling at least part of said hydrocarbon-rich phase to said reaction zone.

18. A process as recited in claim 16, further comprising:
recycling at least part of said isoparaffin-comprising stream to said reaction zone.

19. A process as recited in claim 16, further comprising:
recycling at least part of said solids-depleted effluent to said reaction zone.

20. A process as recited in claim 16, further comprising:
recycling a part of said alkylate-comprising effluent to said reaction zone.

21. A process as recited in claim 16, further comprising:
rejuvenating said solids-depleted effluent by adding hydrogen chloride into said solids-depleted effluent.

22. A process as recited in claim 16, wherein the solids are removed by centrifugation and the amount of solids removed is such that said reaction zone comprises from 0.05 to 5 wt % solids, based on the total weight of said acidic ionic liquid catalyst contained in said reaction zone.

23. A process as recited in claim 17, further comprising:
recycling at least part of said isoparaffin-comprising stream to said reaction zone.

24. A process as recited in claim 17, further comprising:
recycling at least part of said solids-depleted effluent to said reaction zone.

25. A process as recited in claim 17, further comprising:
recycling a part of said alkylate-comprising effluent to said reaction zone.

26. A process as recited in claim 17, further comprising:
rejuvenating said solids-depleted effluent by adding hydrogen chloride into said solids-depleted effluent.

27. A process as recited in claim 17, wherein the amount of solids of said alkylate-comprising effluent that is withdrawn from said reaction zone is such that said reaction zone comprises from 0.1 to 2 wt % solids, based on the total weight of said acidic ionic liquid catalyst contained in said reaction zone.

28. A process as recited in claim 18, further comprising:
recycling at least part of said solids-depleted effluent to said reaction zone.

29. A process as recited in claim 18, further comprising:
recycling a part of said alkylate-comprising effluent to said reaction zone.

30. A process as recited in claim 18, further comprising:
rejuvenating said solids-depleted effluent by adding hydrogen chloride into said solids-depleted effluent.

31. A process as recited in claim 18, wherein the amount of solids of said alkylate-comprising effluent that is withdrawn from said reaction zone is such that said reaction zone comprises from 0.05 to 5 wt % solids, based on the total weight of said acidic ionic liquid catalyst contained in said reaction zone.

32. A process as recited in claim 19, further comprising:
recycling a part of said alkylate-comprising effluent to said reaction zone.

33. A process as recited in claim 19, further comprising:
rejuvenating said solids-depleted effluent by adding hydrogen chloride into said solids-depleted effluent.

34. A process as recited in claim 19, wherein the amount of solids of said alkylate-comprising effluent that is withdrawn from said reaction zone is such that said reaction zone comprises from 0.05 to 5 wt % solids, based on the total weight of said acidic ionic liquid catalyst contained in said reaction zone.

35. A process as recited in claim 19, further comprising:
rejuvenating said solids-depleted effluent by adding hydrogen chloride into said solids-depleted effluent.

36. A process as recited in claim 19, wherein the amount of solids of said alkylate-comprising effluent that is withdrawn from said reaction zone is such that said reaction zone comprises at most 2 wt % solids, based on the total weight of said acidic ionic liquid catalyst contained in said reaction zone.

37. A process for preparing an alkylate, wherein said process comprises:
contacting in a reaction zone and under alkylation conditions a hydrocarbon mixture comprising at least an isoparaffin and an olefin with an acidic ionic liquid catalyst to form within said reaction zone alkylate and solids;
withdrawing from said reaction zone an alkylate-comprising effluent wherein at least a part thereof is a solids-comprising effluent, which includes solids, hydrocarbons, and acidic ionic liquid catalyst; and
removing at least part of the solids from at least part of said alkylate-comprising effluent by means for removing solids therefrom to thereby obtain a solids-depleted effluent, wherein the amount of solids removed from the alkylate-comprising effluent is sufficient to maintain the concentration of solids in the reaction zone at the most 5 wt %, based on the total weight of the acidic ionic liquid catalyst in the reaction zone.

38. A process as recited in claim 37, further comprising:
prior to the step for removing at least part of the solids from said at least part of said alkylate-comprising effluent, separating said at least part of said alkylate-comprising effluent into a hydrocarbon-rich phase and an acidic ionic liquid catalyst-rich phase, wherein said acidic ionic liquid catalyst-rich phase includes said at least a part of said solids-comprising effluent; and
passing at least part of said acidic ionic liquid catalyst-rich phase in place of said alkylate-comprising effluent to means for removing solids therefrom to obtain said solids-depleted effluent, wherein the amount of solids removed from the acidic ionic liquid catalyst-rich phase is sufficient to maintain the concentration of solids in the reaction zone is from 0.05 to 5 wt %, based on the total weight of the acidic ionic liquid catalyst in the reaction zone.

39. A process as recited in claim 38, wherein the means for removing solids is a centrifuge, and further comprising:
fractionating at least part of said hydrocarbon-rich phase to provide an alkylate-comprising product and an isoparaffin-comprising stream.

40. A process as recited in claim 39, further comprising:
recycling at least part of said hydrocarbon-rich phase to said reaction zone.

41. A process as recited in claim 39, further comprising:
recycling at least part of said isoparaffin-comprising stream to said reaction zone.

42. A process as recited in claim 39, further comprising:
recycling at least part of said solids-depleted effluent to said reaction zone.

43. A process as recited in claim 39, further comprising:
recycling a part of said alkylate-comprising effluent to said reaction zone.

44. A process as recited in claim 39, further comprising:
rejuvenating said solids-depleted effluent by adding hydrogen chloride into said solids-depleted effluent.

45. A process as recited in claim 39, wherein the amount of solids of said alkylate-comprising effluent that is withdrawn from said reaction zone is such that said reaction zone comprises from 0.1 to 2 wt % solids, based on the total weight of said acidic ionic liquid catalyst contained in said reaction zone.

* * * * *